United States Patent [19]

Xu et al.

[11] Patent Number: 5,326,690
[45] Date of Patent: Jul. 5, 1994

[54] OVARIAN CANCER ASCITES FACTOR, IN ISOLATED FORM

[75] Inventors: Yan Xu, Brampton; Anne E. Goodbody, Toronto, both of Canada

[73] Assignee: Allelix Biopharmaceuticals Inc., Mississauga, Canada

[21] Appl. No.: 130,239

[22] Filed: Oct. 1, 1993

Related U.S. Application Data

[62] Division of Ser. No. 41,974, Apr. 2, 1993, Pat. No. 5,277,917.

[51] Int. Cl.$^5$ .......................... C12Q 1/02; C12Q 1/00; G01N 33/566; A61K 31/66
[52] U.S. Cl. ...................................... 435/29; 435/7.23; 436/501; 436/64; 436/71; 514/75; 554/78
[58] Field of Search ................. 435/7.23, 29, 240.2, 435/240.3; 424/537, 559, 573; 554/1, 8, 20, 68, 70, 78, 79, 80, 81, 82, 83, 21; 436/71, 501, 63, 64; 514/75, 119, 120, 134, 143

[56] References Cited

PUBLICATIONS

Bligh et al, "A Rapid Method of Total Lipid Extraction and Purification", Can. J. Biochem. Physiol., 1959, 37:911.
Buick et al, "Comparative Properties of Five Human Ovarian Adenocarcinoma Cell Lines", Cancer Research, 1985, 45:3668.
Mills et al, "A Putative New Growth Factor in Ascitic Fluid from Ovarian Cancer Patients: Identification, Characterization, and Mechanism of Action", Cancer Research, 1988, 48:1066.
Mills et al, "Role of Growth Factors: Their Receptors and Signalling Pathways in the Diagnosis, Prognosis, follow-up and Therapy of Ovarian Cancer", Diagn. Oncol., 1992, 2:39.
Mills et al, "Regulation of Growth of Human Ovarian Cancer Cells", Ovarian Cancer 2: Biology Diagnosis and Management (Eds. Sharp, et al) Chapman and Hall Medical, London, 1992, pp. 127-143.
Mills et al, "Regulatory Mechanisms in Ascitic Fluid", Ovarian Cancer: Biologic and Therapeutic Challenges, (Eds. F. Sharp et al) Chapman and Hall Medical, London, 1989, pp. 55-62.
Mills et al, "Ascitic Fluid from Human Ovarian Cancer Patients Contains Growth Factors Necessary for Intraperitoneal Growth of Human Ovarian Cancer Cells", J. Clin. Invest., 1990, 86: 851.
Schact, "Extraction and Purification of Polyphosphoinositides", Methods Enzymol., 1981, 72:626.

*Primary Examiner*—Jeffrey E. Russel
*Assistant Examiner*—Nancy J. Gromet
*Attorney, Agent, or Firm*—Foley & Lardner

[57] ABSTRACT

Herein described is an ovarian cancer activating factor that has been isolated from ovarian cancer ascites fluid. The factor may be utilized in its isolated form in a screening program aimed at identifying inhibitors of factor-mediated ovarian cancer activation, or as a growth supplement useful for culturing ovarian and other cancer cell lines.

1 Claim, 3 Drawing Sheets

OVARIAN CANCER ASCITES FACTOR, IN ISOLATED FORM

This application is a division of application Ser. No. 08/041,974, filed Apr. 2, 1993, now U.S. Pat. No. 5,277,917.

The cause of proliferation of human ovarian cancer tumor cells, the primary cause of death from gynecologic tumors, has not been determined. Abnormal oncogene expression or action has been detected, suggesting that a growth factor might be involved in the growth of ovarian cancer. This had prompted investigation of ascitic fluid for growth factors responsible for proliferation of ovarian cancer cells.

Mills et al (Cancer Research, 1988, 48: 1066) report that ascites fluid taken from ovarian cancer patients, contains a factor that induces proliferation of fresh ovarian cancer cells and the ovarian cancer cell line designated HEY. The proliferative response was associated with rapid increases in phospholipid hydrolysis and changes in intracellular calcium. Evidence presented by these authors suggests that the factor is proteinaceous in nature, having been enriched by application of protein isolation techniques such as ammonium sulphate precipitation, having shown susceptibility to protease K, and having shown susceptibility to boiling. It was later suggested that the factor is a 30 kD glycoprotein (Diagn. Oncol, 1992, 2: 39).

It is an object of the present invention to isolate a factor that is capable of stimulating calcium release in ovarian cancer cells.

SUMMARY OF THE INVENTION

There has now been isolated a factor that activates ovarian cancer cells by stimulating the release of intracellular calcium. In contrast to the findings previously reported, the present ovarian cancer ascites factor, herein referred to as OCAF, is substantially devoid of protein and peptide, and likely is phospholipid in nature. In its isolated form, the factor can be exploited in a screening program aimed at identifying substances that inhibit factor-mediated ovarian cancer activation, for therapeutic use in the treatment of ovarian cancer. Alternatively, the factor may be used as an immunogen, for the purpose of raising antibodies for use therapeutically to inhibit OCAF action in vivo, or for use in detecting OCAF in serum samples for the purpose of ovarian cancer diagnosis.

More particularly, and in accordance with one aspect of the present invention, there is provided a factor that is recoverable from ovarian cancer ascites fluid and that stimulates intracellular calcium release within ovarian cancer cells, wherein the factor is substantially free from proteins and peptides. The factor may be characterized further by (1) solubility in 80% acetone and in 100% methanol; (2) retained activity after boiling in water for up to fifteen minutes, and after incubation with protease; and (3) abolished activity after incubation with Vibrio sp. phospholipase B, with Streptomyces chromofuscus phospholipase D and with soybean lipoxidase.

According to another aspect of the present invention, there is provided a method for obtaining the isolated factor, which comprises the steps of (1) obtaining ovarian cancer ascites fluid;

(2) extracting the fluid with methanol and chloroform;

(3) recovering the aqueous methanol phase and re-extracting with acidified chloroform and methanol;

(4) recovering the chloroform phase and subjecting the chloroform phase to fractionation by silica gel; and (5) recovering the methanol eluant therefrom.

These and other aspects of the present are now described in greater detail with reference to the accompanying drawings in which:

REFERENCE TO THE DRAWINGS

FIGS. 1A and 1B illustrate the effect of OCAF and thrombin on $[Ca^{++}]_i$ release in HEY cells. $[Ca^{++}]_i$ response to sequential addition of OCAF (10 μl) and thrombin (0.1 U)(A); or addition of thrombin followed by OCAF (B);

FIGS. 2A and 2B illustrate cross inhibition of the $[Ca^{++}]_i$ response induced by OCAF and LPA administered in sequence. (A) The trace shows the $[Ca^{++}]_i$ response triggered by OCAF (10 μl), which inhibits the $[Ca^{++}]_i$ response to subsequent addition of OCAF (20 μl) and LPA (10 μM); (B) LPA (10 μM) was added, followed by additional LPA (20 μM) and OCAF (10 μl); and FIGS. 3A and 3B illustrate cross inhibition of the $[Ca^{++}]_i$ response induced by OCAF and SPC administered in sequence. (A) The trace shows the $[Ca^{++}]_i$ response triggered by OCAF (10 μl), which inhibits the $[Ca^{++}]_i$ response to subsequent addition of OCAF (20 μl) and SPC (10 μM); (B) SPC (10 μM) was added, followed by additional SPC (20 μM) and OCAF (10 μl).

DETAILED DESCRIPTION OF THE INVENTION

Figure 1A:
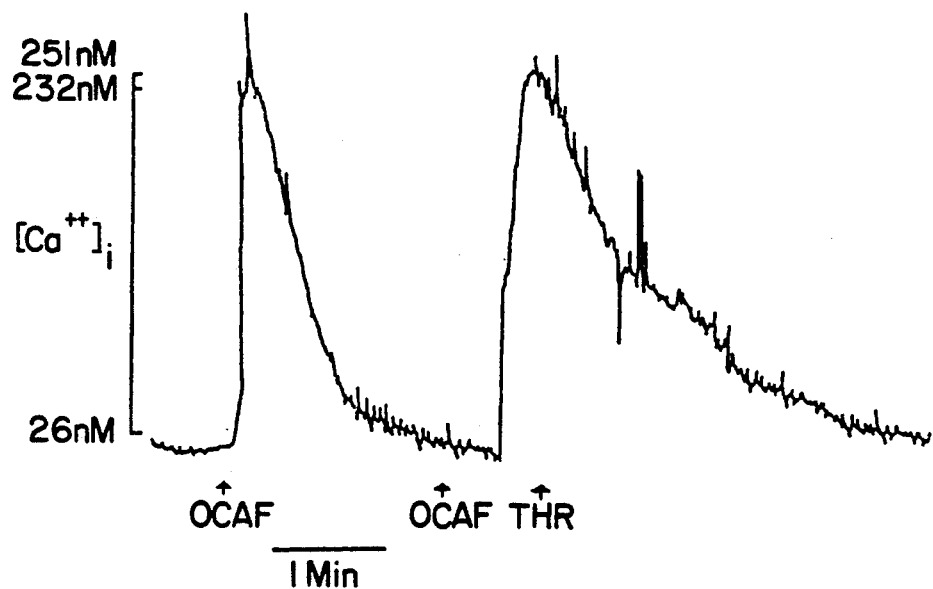

The invention relates to an isolated factor, designated OCAF, that activates ovarian cancer cells, by stimulating the release of intracellular calcium. The term "isolated" is used herein with reference to a factor that is substantially free from proteins and peptides, i.e. is free from proteins and peptides detectable by protein staining techniques. The activating property of the factor with respect to ovarian cancer cells is revealed using the fluorescence scanning technique and the incubation protocol reported by Mills et al, supra, which is incorporated herein by reference. Briefly, established ovarian cancer cells, of the line designated HEY, are preincubated with the fluorescing calcium chelator Indo-1; after addition of the factor, the cells are scanned using a spectrophotometer to measure chelated calcium and thus indirectly measure the increased concentration of intracellular calcium.

The various identifying characteristics of the ovarian cancer ascites factor of the present invention were revealed upon examination of a preparation obtained from ascites fluid that was taken from ovarian cancer patients. The preparation was obtained in the manner described in example 1 herein. Briefly, this entailed a first methanol/chloroform extraction of fresh human ovarian cancer ascites fluid according to the method described by Bligh and Dyer in Can. J. Biochem. Physiol., 1959, 37: 911. The OCAF activity was recovered in the aqueous/methanol phase, which was re-extracted with acidified chloroform and methanol according to the method described by Schact in Methods Enzymol., 1981, 72: 626. The factor-containing chloroform phase was then fractionated on silica gel, and the isolated OCAF was eluted using methanol.

The factor resulting from this extraction was subjected to various analytical techniques, and its ovarian cancer activating properties were compared with other known activating and growth factors, using the HEY-based fluorescence scanning assay. As is revealed in the examples which follow, OCAF is probably lipid in nature, and may be a unique form of phospholipid.

In its extracted form, OCAF may be exploited in screening assays designed to identify compound(s) that inhibit OCAF-mediated activation of ovarian cancer cells. Such an assay entails incubating an ovarian cancer cell line, such as the HEY cell line, in the presence of OCAF and a compound the inhibiting properties of which are to be determined. Inhibition by the compound will be revealed by elimination of or a reduction in the intracellular release of calcium within the ovarian cancer cell line, relative to a control experiment in which only OCAF is present.

Inhibitors of OCAF may be in the form of antibodies, raised by immunizing rabbits, for instance, with OCAF and then recovering the antibodies so formed according to well established procedures. When conjugated to a reporter such as an enzyme, e.g. urease, peroxidase and the like, such antibodies can also be exploited to determine the presence of OCAF in biological samples, as a way of diagnosing ovarian cancer.

EXAMPLE 1

Isolation of the Factor

Freshly obtained ascites was centrifuged to remove cells. 25 ml of methanol and 12.5 ml of chloroform were added to 10 ml of ascites. After thorough mixing of their contents, the mixture was centrifuged (1000 g, 10 min). The supernatant was removed to a new tube and the precipitate was re-extracted with 12.5 ml of chloroform. The combined supernatant was washed with 12.5 ml of 0.88% KCl in $H_2O$ and separated into two layers by centrifugation. The precipitate, which contained more than 99% protein (determined by the Bio-Rad protein assay), had no OCAF activity and was discarded. The lower chloroform phase, which contained mostly neutral lipids (revealed by TLC analysis), had no OCAF activity. The upper aqueous/methanol layer contained OCAF activity (~90% activity from crude ascites). The methanol and most of the $H_2O$ in this phase was removed by a rotary evaporator at 50° C. The resulting material was brought up to 1 ml by $H_2O$ and 3 ml of chloroform/methanol (1:2) was added and mixed. Then, 1 ml of 2.4N HCl and 1 ml chloroform were added. After thorough mixing, the mixture was centrifuged (about 1000 g for 10 min) and the lower layer was transferred into new tubes. The interface and upper phase were extracted once more with 2 ml of chloroform. The combined lower phases were washed with 4 ml of methanol-1N HCl, 1:1 (v/v). The upper phase, found to contain no OCAF activity, was discarded after centrifugation. The lower layer was collected, and found to possess OCAF activity (>80% recovery from crude ascites).

OCAF in this acidified chloroform was passed on a Sep-Pak silica cartridge (~10 ml/cartridge), which was washed with 20 ml of chloroform, 20 ml of acetone and then 20 ml of chloroform/methanol(50:50, v/v). The OCAF activity was eluted with 50 ml of methanol with overall recovery >70%.

This OCAF preparation is free of protein and amino acid, as assessed by silver-stained SDS PAGE and TLC analysis by staining with ninhydrin. TLC analysis also indicated that OCAF is substantially free of neutral lipids.

EXAMPLE 2

Evaluation of the Factor

The activating properties of OCAF and various comparison compounds were investigated by determining increases in the intracellular calcium concentration within HEY cells. For this purpose, HEY cells (a human ovarian cancer cell line obtained from Toronto General Hospital) having the properties described by Buick et al, Cancer Research, 1985, 45:3668) were cultured in complete medium (RPMI 1640 (GIBCO, Grand Island, N.Y.) substituted with 5% (v/v) FCS (Flow Laboratory, Maclean, Va.), 2 mM glutamine (GIBCO) and $1 \times 10^5 M$ mercaptoethanol. Cells were split weekly and were cultured in RPMI 1640 without FCS for at least 20 hours prior to use. Cells were harvested in PBS, 2 mM EDTA.

Measurements of intracellular calcium were obtained as described by Mills et al, supra, using Indo-1-AM as the $Ca^{++}$ chelator and fluorescence indicator. HEY cells were loaded with Indo-I AM, washed and incubated at 37° C. for at least 30 min. Different compounds were added to the cells at concentrations as indicated and fluorescence changes were measured by a Hitachi 4000 spectrophotometer at 37° C. Ascites was used as a positive control to show that the cells were responsive. In all cases, assays were performed in a calcium free buffer (140 mM NaCl, 1 mM KCl, 1 mM $MgCl_2$, 10 mM glucose, and 20 mM HEPES, pH 7.23) and 1 mM EGTA was added followed by the test samples.

To confirm that various known growth factors were not responsible for OCAF activity, the factors identified in Table 1 were evaluated in the HEY-based assay at the noted concentrations.

TABLE I

| PEPTIDE GROWTH FACTORS TESTED IN [$Ca^{++}$]$_i$ ASSAY | | |
|---|---|---|
| COMPOUND | CONCENTRATION | ASSAY($Ca^{++}$) |
| TGF-α | 0.01 ng-1 μg/ml | — |
| TGF-β | 100 ng/ml | — |
| EGF | 0.01 ng-1 μg/ml | — |
| Acidic FGF | 0.01 ng-1 μg/ml | — |
| Basic FGF | 0.01 ng-1 μg/ml | — |
| PDGF | 5 ng/ml | — |
| IGF-I | 0.01 ng-1 μg/ml | — |
| IGF-II | 0.01 ng-1 μg/ml | — |
| IL-1 | 1,000 half-max. units/ml | — |
| IL-2 | 0.01 ng-1 μg/ml | — |
| IL-8 | 0.01 ng-1 μg/ml | — |
| TNF-α | 100 ng/ml | — |
| INSULIN | $10^{-6}$ M | — |
| LIF* | 0.01-1 μg/ml | — |
| THROMBIN | 0.1-10 unit/ml | + |
| FIBRINOGEN | 2-200 μg/ml | — |
| VASOPRESSIN | 100 ng/ml | — |
| ANGIOTESIN | 100 ng/ml | — |
| α- & β-INTERFERONS | 10,000 units/ml | — |
| BOMBESIN | 10 nM-1 μM | — |
| BRADYKININ | 10 nM-1 μM | — |
| PHA** | 30 μg/ml | — |

*LIF: Leukaemia Inhibitory factor
**PHA: Mitogenic lectin phytohemagglutinin

Figure 1B:
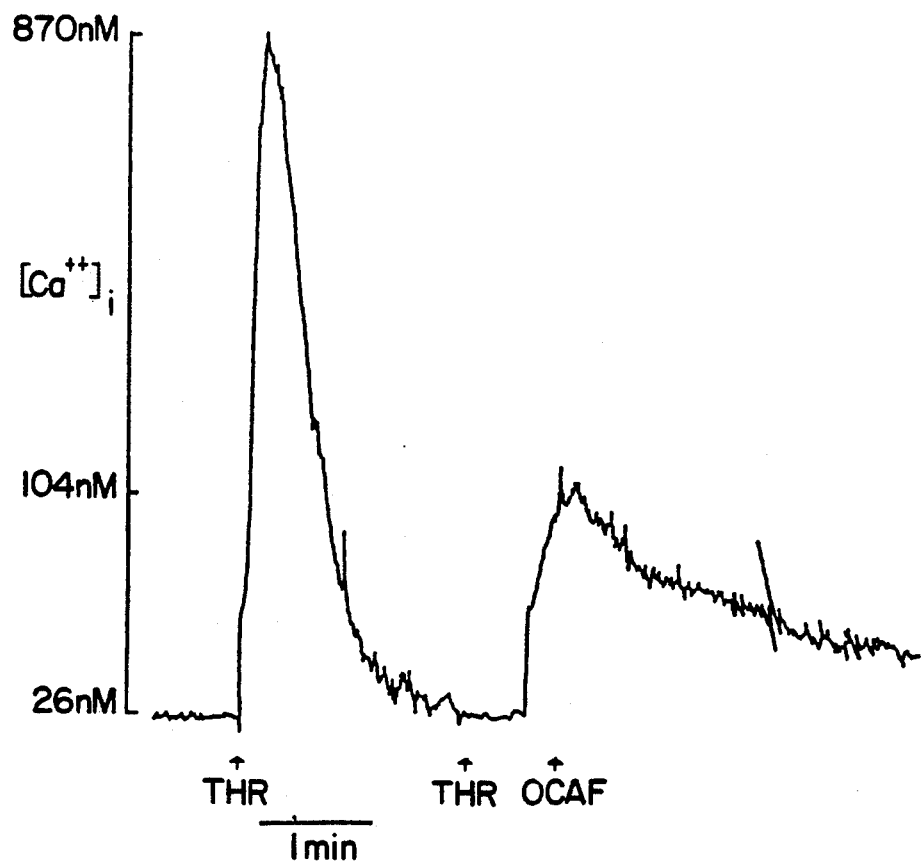

Of the more than 20 different peptide growth factors tested, only thrombin stimulated a transient [$Ca^{++}$]$_i$ increase in HEY cells. However, thrombin did not interfere with the OCAF-activated calcium signal, although some attenuation did occur (FIGS. 1A and 1B).

Furthermore, antithrombin was found to block thrombin activity, but not OCAF activity.

Still further evidence that OCAF is not a protein was obtained from protease digestion studies. It was found that OCAF activity was not abolished after treatment with the following proteases, all of which were separately incubated with OCAF at 37° C. for 3–5 hours: bromelain, carboxypeptidase Y, peptidase, pepsin, papain, protease types XXV (Pronase E), XVII-B (V8), XIII and XIV (pronase E), proteinase K, thermolysin, and trypsin.

Further characterization of OCAF also demonstrated that it is resistant to extremely harsh treatment including boiling in water for fifteen minutes, extremes of pH and detergent treatment. Furthermore, it is soluble in 80% acetone and 100% MeOH, suggesting that it could be a lipid. More than 20 known lipid growth factors/mediators were then tested, and the results are presented in Table II.

TABLE II

ORGANIC COMPOUNDS TESTED IN [Ca++]; ASSAY

| COMPOUND | CONCENTRATION | ASSAY (Ca++) |
|---|---|---|
| ARACHIDONIC ACID | 12, 24, 60, 120, 480 μM | − |
| OLEIC ACID | 1, 12, 120 μM | − |
| DIACYLGLYCEROL | 1, 12, 20, 200 μM | − |
| PHOSPHATIDIC ACID | 12, 60 μM | − |
| PHOSPHATIDYL-CHOLINE | 12, 30, 75, 300 μM | − |
| PHOSPHATIDYL-ETHANOLAMINE | 12, 30, 80 μM | − |
| PHOSPHATIDYL-SERINE | 12, 30, 80 μM | − |
| **LPA | 1, 12 μM | + |
| LPC | 12, 60 μM | − |
| LPE | 1, 12, 20 μM | − |
| LPG | 1, 12, 20, 50 μM | − |
| LPI | 1, 12, 20, 50 μM | − |
| **LPS | 1, 12 μM | + |
| SPHINGOSINE | 1, 12, 20, 50 μM | − |
| **SPC | 1, 12, 20 μM | + |
| SPHINGOMYELIN | 1, 12, 20 μM | − |
| OSM | 2, 10, 20 μM | − |
| CERAMIDE | 1, 12, 20 μM | − |
| PAF | $10^{-11}$ TO $10^{-5}$ M | − |
| TPA | $10^{-10}$ TO $10^{-6}$ M | − |
| CARBACHOL | 0.2, 1.2, 2.4 mM | − |

Figure 2A:
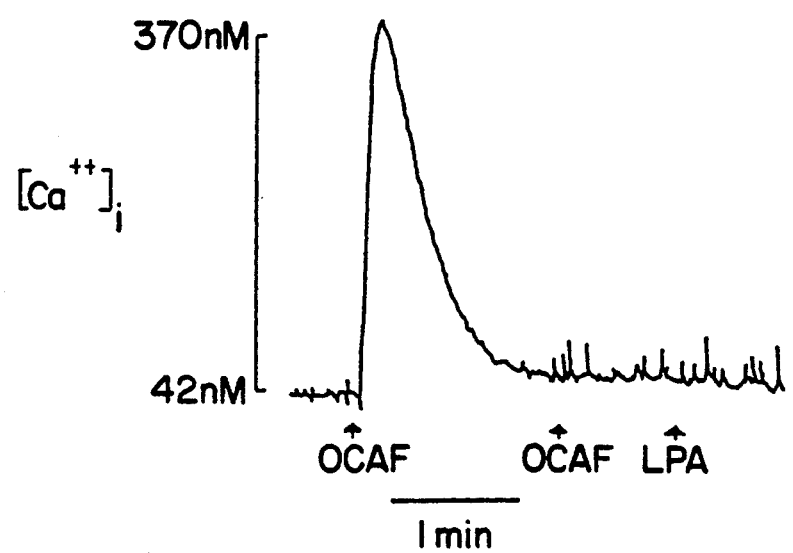
Figure 2B:
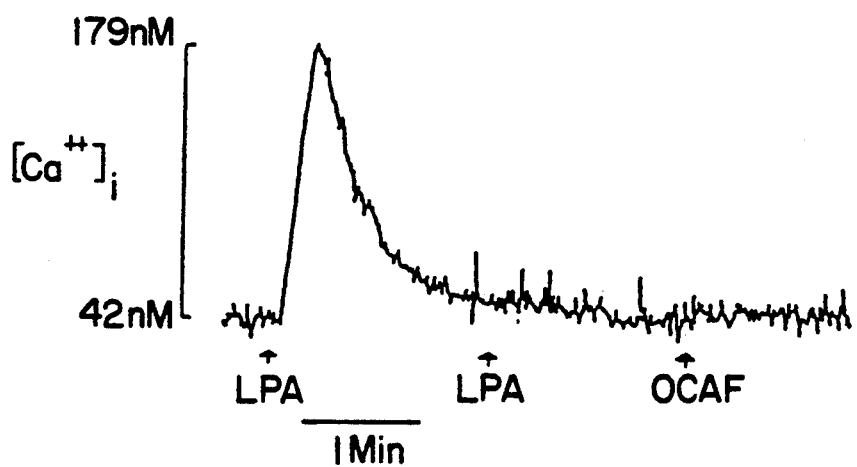
Figure 3A:
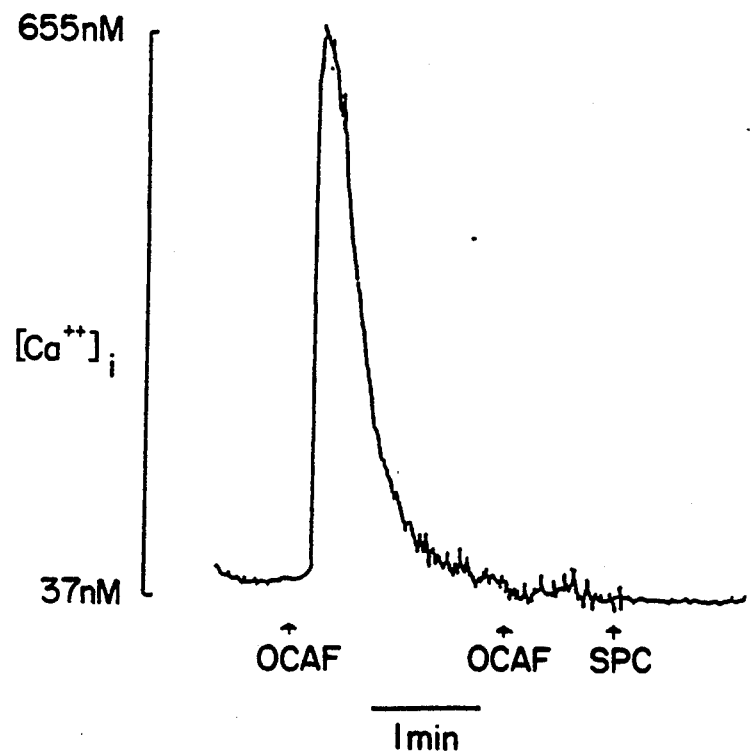
Figure 3B:
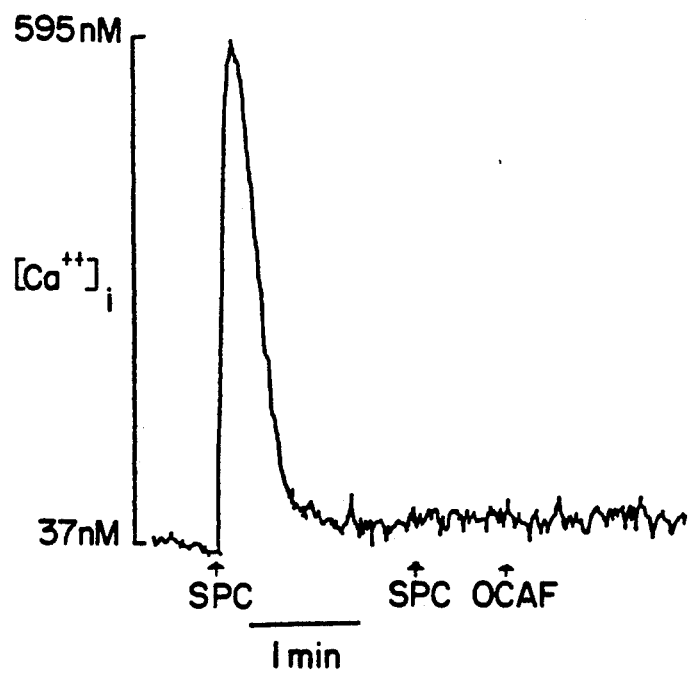

LPA: Lysophosphatidic acid (oleoyl, palmitoyl or stearoyl)
LPC: L-α-lysophosphatidylcholine (oleoyl or palmitoyl)
LPE: Lysophosphatidylethanolamine (oleoyl)
LPG: Lysophosphatidylglycerol
LPI: Lysophosphatidylinositol
LPS: Lysophosphatidylserine
SPC: Sphingosylphosphorylcholine
OSM: N-oleoyl-D-sphingomyelin
PAF: Platelet activating factor
TPA: 12-O-tetradecanoylphorbol-13-acetate It will be seen from Table II that LPA (oleoyl, palmitoyl, and stearoyl), LPS and SPC were found to stimulate [Ca++]$_i$ release in HEY cells. Furthermore, they all cross inhibit OCAF and each other in the assay and FIGS. 2 and 3 show typical interactions. Enzymatic digestions of OCAF and other lipids were carried out to determine whether OCAF is phospholipid in nature, and whether other phospholipids might possess OCAF activity. Phospholipase digestions were carried out in 10 mM HEPES, pH 7.4, with either 100 mM NaCl or 4 mM CaCl$_2$ at 37° C. for 3 h. The reactions were stopped by freezing at −20° C. No further extraction was done and the mixtures were assayed for calcium release activity as described above. The enzymes used were also incubated in the absence of substrate under the same conditions, and no calcium release was observed. The results are shown in Table III.

TABLE III

[Ca++]; RELEASE AFTER ENZYMATIC DIGESTIONS

| SAMPLE | CONTROL | PL-B | PL-D | LIPOXIDASE |
|---|---|---|---|---|
| OCAF | ++ | − | − | − |
| LPA | ++ | − | ++ | ++ |
| LPC | − | − | ++ | − |
| LPS | ++ | − | ++ | − |
| SPC | ++ | ++ | − | ++ |
| Thrombin | ++ | ++ | ++ | ++ |

LPA: Lysophosphatidic acid (oleoyl, palmitoyl or stearoyl)
LPC: Lysophosphatidylcholine (oleoyl or palmitoyl)
LPS: Lysophosphatidylserine (mainly stearoyl)
SPC: Sphingosylphosphorylcholine
PL-B: Phospholipase B (Vibrio species)
PL-D: Phospholipase D, type VI (Streptomyces chromofuscus)
LIPOXIDASE: Lipoxidase (soybean)

The digestion profile of OCAF does not correspond to those observed for other phospholipids, but imply structural similarity. Judging from its sensitivity to phospholipase B and D, OCAF is likely a phospholipid other than LPA, LPS and SPC.

We claim:

1. A screening method useful for identifying compounds capable of inhibiting an ovarian cancer cell factor, which method comprises the steps of:
    (1) incubating (a) a factor which is free of proteins and peptides, which is recoverable from ovarian cancer ascites fluid, and which stimulates intracellular calcium release within ovarian cancer cells, with (b) a candidate inhibitor of said factor, and (c) a factor-responsive cell-line; and
    (2) determining the effect of said candidate inhibitor on the intracellular calcium levels within said factor-responsive cell-line, whereby the inhibitory effect of the candidate inhibitors is revealed.

* * * * *